United States Patent [19]

Weiss et al.

[11] 4,144,373
[45] Mar. 13, 1979

[54] MATERIALS FOR THE SEPARATION OF ORGANIC SUBSTANCES FROM SOLUTION

[75] Inventors: Donald E. Weiss, Blackburn; David R. Dixon, Keilor; Simon M. West, Williamstown, all of Australia

[73] Assignees: Commonwealth Scientific and Industrial Research Organization, Campbell; Kraft Foods Ltd., Port Melbourne, both of Australia

[21] Appl. No.: 753,908

[22] Filed: Dec. 23, 1976

[30] Foreign Application Priority Data

Dec. 24, 1975 [AU] Australia .............................. 4398/75

[51] Int. Cl.$^2$ ............................................. B32B 5/18
[52] U.S. Cl. ................................... 428/306; 210/502; 252/428; 252/430; 428/309; 428/323; 428/329; 428/408
[58] Field of Search ............... 428/304, 305, 306, 307, 428/308, 309, 323, 329, 408; 252/428, 430, 62.51; 210/36, 425, 502

[56] References Cited

U.S. PATENT DOCUMENTS

| | | | |
|---|---|---|---|
| 3,803,033 | 4/1974 | Sutherland | 210/40 |
| 3,850,843 | 11/1974 | Kunugi et al. | 252/428 |
| 3,925,248 | 12/1975 | Moroni et al. | 252/428 |
| 3,953,360 | 4/1976 | Morihita et al. | 252/428 |
| 3,974,227 | 8/1976 | Berthoux | 252/428 |
| 4,028,269 | 6/1977 | Carlson | 252/428 |
| 4,046,939 | 9/1977 | Hart | 428/311 |

*Primary Examiner*—James J. Bell
*Attorney, Agent, or Firm*—Kenyon & Kenyon

[57] ABSTRACT

A selective adsorbent for the separation of organic material from solution comprises adsorbent particles and magnetic particles embedded in a porous matrix of organic polymeric material, the porosity of the matrix being selected so as to allow only molecules of up to a certain order of molecular weight to enter into the interstitial structure of the matrix whereby the composite material functions selectively to adsorb dissolved materials from solution. The adsorbent is useful, inter alia, in the food processing industry where trace quantities of materials need to be separated from complex mixtures.

16 Claims, 2 Drawing Figures

AMOUNT OF RIBOFLAVIN ADSORBED PER GRAM OF ADSORBENT AFTER 3 HOURS EQUILIBRATION AS A FUNCTION OF THE DEGREE OF CROSS LINKING.

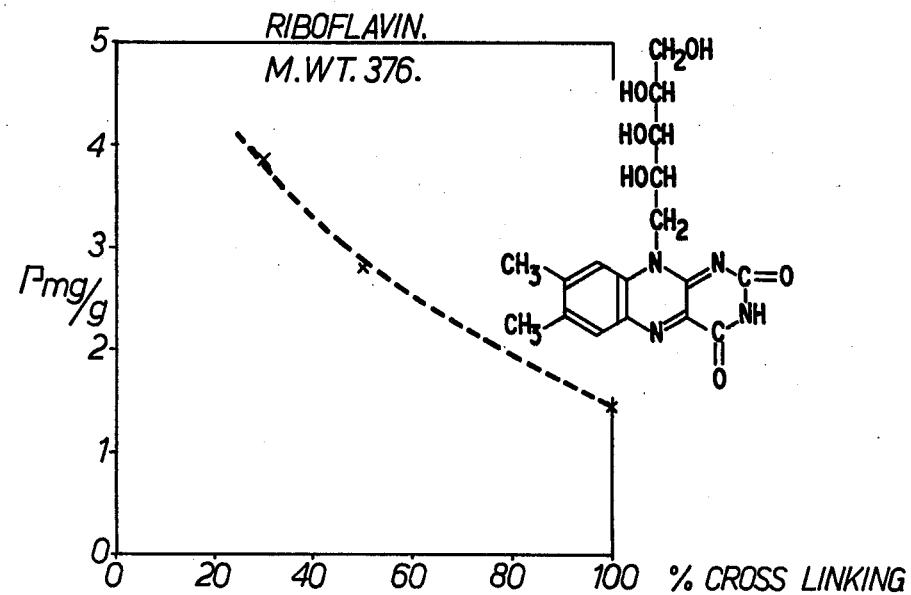
FIG.1: AMOUNT OF RIBOFLAVIN ADSORBED PER GRAM OF ADSORBENT AFTER 3 HOURS EQUILIBRATION AS A FUNCTION OF THE DEGREE OF CROSS LINKING.
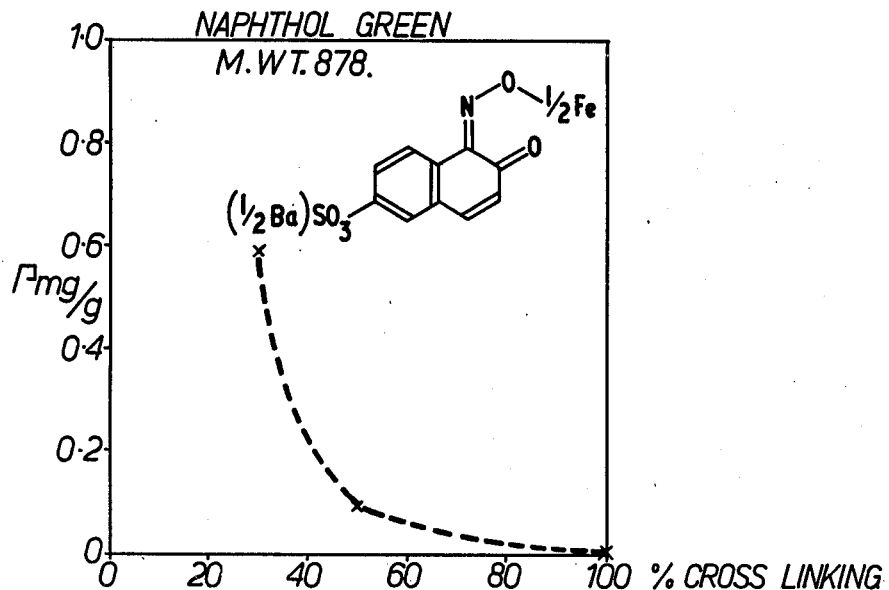
FIG.2: AMOUNT OF NAPHTHOL GREEN ADSORBED PER GRAM OF ADSORBENT AFTER 24 HOURS EQUILIBRATION AS A FUNCTION OF THE DEGREE OF CROSS LINKING.

MATERIALS FOR THE SEPARATION OF ORGANIC SUBSTANCES FROM SOLUTION

This invention relates to improved materials which are useful for the separation of small quantities of organic material from solution.

It is well known that dissolved materials can be adsorbed from solution using solid particles which have suitable surfaces. Foremost in such adsorbing materials is activated carbon which is used extensively throughout the chemical and process industries. Other materials with such properties include various clays and other mineral powders. The adsorption process involves the physical attachment of the dissolved material to the particle surfaces and is a reversible process in that the adsorbed material can usually be removed through treatment in a suitable way.

Generally such adsorption is relatively non-selective and in a mixture of materials, the adsorbent will remove part or all of such materials. It is therefore a process usually not suited to the removal of one particular constitutent of a solution, either an unwanted impurity or a desired compound which occurs in small quantity. In many cases, therefore, a more selective adsorbent is required.

Another disadvantage of adsorption with carbon and other adsorbents is the difficulty in separating the adsorbent from other solid, undissolved materials present in the system. Thus, it is often desired to remove a small amount of dissolved material from a mixture which contains suspended products, without removing such suspended products, and solid adsorbents of known type do not lend themselves to such a process.

It is therefore an object of this invention to provide an adsorbent material which will separate small quantities of dissolved material from a solution, while not affecting other dissolved or undissolved products. It is a further object to provide an adsorbent material which can be separated from a mixture of dissolved and undissolved material.

The objects of the invention are achieved by providing a composite material which is porous and includes an adsorbent in such a way that the product to be separated from a solution will diffuse into the composite material and be adsorbed within the composite. At the same time, larger unwanted molecules will be excluded from entering the material. Furthermore, the composite material is made so as to include magnetic particles whereby the composite may be easily and rapidly separated from the mixture after adsorption has taken place.

BRIEF DESCRIPTION OF THE DRAWING

The FIGS. 1 and 2 illustrate in graphical form the influence of the degree of crosslinking of the hydrophilic polymer on the porosity of the polymer comprising the composite adsorbent of this invention, as demonstrated by the experiment reproduced in Example 16.

According to the invention, there is provided a composite material comprising adsorbent particles and magnetic particles embedded in a porous matrix of organic polymeric material, the porosity of the matrix being selected so as to allow only molecules of up to a certain order of molecular weight to enter into the interstitial structure of the matrix whereby the composite material functions selectively to adsorb dissolved materials from solution.

One form of the invention resides in a composite material comprising adsorbent particles and magnetic particles embedded in a porous matrix of organic polymeric material, the porosity of the matrix being such as to allow small molecules of molecular weight up to several hundred to enter freely into the interstitial structure of the matrix but to exclude larger molecules of higher molecular weight whereby the composite material functions selectively to adsorb dissolved materials from solution. Such larger molecules may for instance, comprise polymers, proteins and the like.

The composite adsorbent material is preferably formed as small fine beads.

The adsorbent particles may comprise carbon, alumina, silica gel, activated magnesium silicate, various clays and mineral powders. Such materials are preferably embedded in the porous matrix in such a way that a large proportion of their surface area retains the capability of adsorbing to be separated.

Suitable matrix materials are hydrophilic polymers such as polyvinyl alcohol, crosslinked with a dialdehyde such as glutaraldehyde; cellulose and certain of its ethers, which may be crosslinked with epichlorhydrin; polyacrylamide or polymethacrylamide, also crosslinked with epichlorhydrin; polyamides such as 6,6-nylon cross-linked with formaldehyde; and polyols such as polyethylene glycol insolubilized by reaction with di-isocyanates.

A large number of substances are available to invest the composite adsorbent material with the desired magnetic properties. As examples of such substances we mention magnetite, gamma iron oxide, and soft or hard ferrites such as "Ferroxdur" (Registered Trade Mark), barium ferrite or "Ferroxcube" (Registered Trade Mark) and spinel ferrite.

In some cases it may be necessary to precoat the magnetic particles with a thin, insoluble and protective layer, such as an organic polymeric material. Such a precoat will prevent iron, for example, from entering the solution by dissolution of the ferromagnetic material during usage of the composite adsorbent material.

Precoating may be achieved, for example, by the vapour phase deposition of a suitable polymer, by an interfacial polymerisation technique, or by immersing the particles in a solution of a preformed polymer and stripping off the solvent. For instance, a coating of poly(paraxylylene) may be achieved by heating "Paralene" (a Registered Trade Mark of Union Carbide Corporation) and permitting the vapour to polymerise at ca. 500° C. on the surface of the magnetic particles. As an example of an interfacial polymerisation technique, hydrophilic magnetic particles may be wetted with an aqueous solution of hexamethylene diamine and then suspended in a hydrocarbon. When an acid dichloride, such as sebacoyl or phthaloyl chloride, is added to the suspension, a polyamide film deposits around the particles. As an example of the solvent technique, ferromagnetic particles having an hydrophobic surface may be coated with polyisoprene, polyisobutylene or cis-polybutadiene by adding the particles to dilute solutions of the polymers in benzene or toluene. After immersion, the solvent is removed, the procedure being repeated until a polymer of suitable thickness is obtained.

Alternatively the ferromagnetic particles may be wetted with a polar polymer, such as a fatty acid modified polyamide, dissolved in a volatile polar solvent and then suspended in a non volatile non polar solvent. Heating the dispersion whilst stirring causes the polar solvent to evaporate thus depositing a polymer film uniformly around the particles. Surfactants are added to control the wetting characteristics and to enable a fine dispersion to be produced.

Treating the surface of the particles with a material, such as trimethylchlorosilane, to give a hydrophobic surface is also effective in minimising corrosion of the particles.

The invention further resides in a method of making a composite material which comprises the steps of mixing adsorbent particles and magnetic particles with a material capable of forming a crosslinked polymer and a crosslinking agent, and controlling the degree to which crosslinking occurs whereby a porous crosslinked polymeric matrix incorporating the adsorbent particles and the magnetic particles is produced in which the pore size is such as to exclude molecules of more than a predetermined order of molecular weight from entering into the interstitial structure of the matrix, the composite material thus being capable of selectively adsorbing dissolved material from solution.

The composite adsorption material may be prepared by crosslinking a suitable polymer to form a matrix of appropriate pore structure in which the magnetic and adsorbent particles are embedded. One such polymer which can be used in this manner is polyvinyl alcohol. Suitable composite adsorbent materials may be made by dissolving polyvinyl alcohol in water and suspending an adsorbent such as carbon together with a magnetic material such as iron oxide coated in the manner described above. A crosslinking agent is added, typically a dialdehyde and an appropriate catalyst to promote the crosslinking. In the case of a dialdehyde, an acid catalyst is suitable but generally the catalyst must be chosen which will promote the crosslinking reaction. Other polymers may be used together with suitable crosslinking agents by means well known to polymer chemists.

In order to achieve suitably sized beads of composite adsorbent material, the mixture prepared above is often best added to an organic liquid which forms a separate phase with water. Through suitable selection of preparative parameters e.g. the nature and concentration of the surface active agent, stirring mode, phase ratio, temperature, pH and rate of gelation, the bead size and shape can be controlled. For example, the preparation of larger spherical particles is favoured by reduced stirring, a low concentration of the surface active agent, cooler temperature, higher pH and a slower rate of gelation. Where the bead size and structure is unimportant, the material may be produced by rapid crosslinking, i.e. low pH, higher temperature, with a lower phase ratio and more rigorous stirring. The final product may then be ground as required.

In some instances, the composite adsorbent material produced in this manner is rather poor in physical properties. This is thought to be due to adsorption of reactants on to the adsorbent particles, thus effectively withdrawing the reactants from the reaction mixture. It has now been found that this effect can be avoided by pretreating the adsorbent particles with a suitable protecting agent. The curing of the matrix will then proceed readily to give a product comprising particles of superior mechanical strength and purity.

The protecting agent should be a material which adsorbs strongly to the adsorbent particles, but which can be readily removed after incorporation in the composite material. The nature of the protecting agent will depend largely on the particular adsorbent being used, but we have found aliphatic acids, e.g. acetic or propionic acid to be particularly useful. Alternative materials are starches, or gelatine, which may be removed by enzymatic means.

In a typical preparation, the adsorbent particles may be slurried with the protecting agent, such as acetic acid and then filtered and washed. Alternatively, spray drying may be used on a mixture of the adsorbent and a starch solution to produce material protected with starch. The fine-coated adsorbent is then added to a dispersion of the polymer to be used as matrix in a suitable solvent (often water) together with the magnetic material and suitable catalysts. This dispersion is then mixed with another solvent of different character, surfactant added to control the interfacial conditions and the crosslinking agent added. The whole mixture is stirred adequately so that the resultant product is in the form of spherical beads. The mode of stirring in conjunction with the nature and concentration of the surfactant controls the size of the beads. Also some control over the size of the matrix pores, and hence over the adsorption specificity of the product, can be achieved through varying the degree of crosslinking of the matrix. Finally, the adsorbent is reactivated by removal of the protective material.

A liquid mixture from which a component is to be separated may be simply mixed or stirred with a composite adsorbent material of the invention until adsorption has taken place. Alternatively the composite adsorbent material may be used as a column through which the liquid mixture is passed, or it may be used in a fluidized bed form in the liquid mixture or in any other way which allows adequate contact of the material with the liquid mixture.

The adsorption stage is followed by a separation stage which permits not only the removal of loaded composite adsorbent material from the liquid but also separation of the adsorbent from the other solid materials present in the process stream. This may be achieved by using a magnetic drum separator, a magnetic filter or a simple settling tank. The magnetic component of the composite adsorbent material confers such properties on the material as rapid sedimentation and response to an applied magnetic field. Such a separation would not be possible with a non-magnetic adsorbent material.

The composite adsorbent material may then be regenerated in any suitable way.

The invention is of particular use in the food and related processing industries, where trace quantities of materials need to be separated from a complex mixture of solid and liquid. It may be necessary to remove any unwanted material which interferes with flavour or it may be desireable to extract materials such as vitamins and the like which occur in small quantity and are difficult to separate.

An example of a process where the composite adsorbent material can be used to solve a problem which can only otherwise be solved with difficulty and loss of product is in the preparation of concentrated yeast extracts. Such extracts are commonly made from brewer's yeast and the flavour is seriously affected by the presence of bitter principles, isohumulones, which occur in very small quantities. Normal methods for removing the principles, such as washing with sodium hydroxide, lead to losses. The composite adsorbent material according to this invention rapidly and easily removes the isohumulones which can be recovered from the adsorbent and is an article of commerce.

Another example of the usefulness of the material according to this invention is in the extraction of riboflavin from cheese whey. Removal of the cheese curd from milk leaves a whey which contains a number of components such as protein, fat lactose and minerals, together with riboflavin in very small quantities. Riboflavin is a valuable material, being an essential vitamin for man and animals. It is an unstable material, which makes its isolation from a mixture such as whey difficult. By treating whey with the adsorbent composite according to this invention, riboflavin may be easily separated and isolated.

The invention is illustrated by the following non-limitative examples.

EXAMPLE 1

Protection of iron oxide with a polyamide coating

Black iron oxide (44g) was added to a solution (32g) of Polymid 55 in propanol (1g to each 2 ml) and stirred thoroughly in an homogenizer vessel. This mixture was then added to Ondina 33 (250 ml) heated to 55° C. and air bubbled through the suspension. The resultant mixture was filtered and the particles washed with hexane to remove oil adhering to the surface. A similar result was obtained using gamma iron oxide instead of black iron oxide.

An alternative method for applying the coating was to inject the propanol/Polymid suspension into the chamber of a spray drier via an atomiser at a temperature and pressure sufficient to evaporate the solvent.

EXAMPLE 2

Protection of iron oxide with a polyvinyl chloride coating

Gamma iron oxide (24g) and Corvic (6g) were mixed thoroughly in acetone (300 ml). This mixture was added to Ondina 33 (300 ml) and isopropyl ammonium dodecylbenzene sulphonate (0.15g), heated to 50° C. and air bubbled through the suspension. After the solvent was evaporated, the suspension was filtered and the product washed with hexane.

EXAMPLE 3

Protection of adsorbent with acetic acid

To aluminium oxide (16g) was added glacial acetic acid (80g). The mixture was then stirred for 30 mins, prior to filtration and washing with distilled water. Thus protected the adsorbent was added to a primary dispersion and as described in later examples, incorporated in the composite material. At this stage, the adsorbent in the magnetic composite was reactivated by washing with copious quantities of 0.3M NaOH and then distilled water until it had been demonstrated that the elutriate was free of acetate ions.

The same method was successfully used to protect activated carbon.

EXAMPLE 4

Protection of the adsorbent with a starch mixture

To carbon (10g) was added pregelatinized waxy maize starch (6g) and cereal solid (24g) and amylase (0.03g) in water (70g). This viscous slurry was then injected via an atomiser into a spray drier and the spherical particles produced were then used in the preparation of a magnetic adsorbent, as described in later examples. The coating was later degraded by the enzyme after activation at pH 8. The degradation products were then removed by washing with methanol and 0.3M sodium hydroxide solution, leaving the composite adsorbent material in an activated state.

EXAMPLE 5

Preparation of a composite adsorbent material using unprotected activated carbon and 10% crosslinking To 20 g of a 15% solution of "GELVATOL 20-30" was added 5 ml of water and sufficient 2 N hydrochloric acid to give a solution pH of 1.5. 6.65 g of Darco G-60 (Trade Mark for an activated carbon) and 6.65 g of gamma iron oxide precoated with a polyamide film was stirred in to give a slurry, and to this was added 0.7 ml of a 25% solution of glutaraldehyde, an amount calculated to react with and crosslink 10% of the hydroxy groups on the polyvinyl alcohol. The mixture was spread over a polyethylene sheet and heated in an air oven at 70° C. for 30 min. The polymer composite was peeled off the plastic sheet, broken up and ground into particles of size 1 mm and smaller, and cured by refluxing in 200 ml of 1 N hydrochloric acid for 4 hr. The product was water washed and air dried.

EXAMPLE 6

Preparation of a composite adsorbent material using acid-protected carbon and 30% crosslinking To Gelvatol 20-30 (13.3% solution in 300 ml) was added carbon (80g) pretreated with glacial acetic acid according to the method of Example 3. Gamma iron oxide (80g) and sufficient hydrochloric acid were added to give a solution pH of 1.5. This slurry was added to a mixture of orthodichlorobenzene (3l) and Span 85 (60g) and the mode of stirring adjusted to provide particles of the desired size and shape. Glutaraldehyde solution (27.3g) was then added, this being the amount deemed necessary to achieve crosslinking of 30% of the hydroxy groups on the polyvinyl alcohol. After one hour the resultant mixture was filtered, washed with acetone and then distilled water and cured by heating in a vacuum oven at 100° C.

EXAMPLE 7

Preparation of a composite adsorbent material using acid-protected silica gel and 100% crosslinking To Gelvatol 20-30 (8g) and gamma iron oxide (16g) was added water (60g). Then silica gel (16g) precoated with acetic acid is described in example 3, was stirred in to give a slurry, and to this was added sufficient concentrated hydrochloric acid to give a solution pH of 1.5. The mixture was added to orthodichlorobenzene (600 ml) and Span 85 (6g) stirred at 1000 rpm with a 3" impeller in a baffled reactor. A solution of glutaraldehyde (18.3g, an amount calculated to react with and crosslink 100% of the hydroxy groups of the polyvinyl alcohol) was added. After stirring in this manner for one hour the slurry was filtered and the product washed with acetone and then distilled water before drying and curing. The composite consisted of spherical beads of size approximately 400 μm.

EXAMPLE 8

Preparation of a composite adsorbent material using starch-protected carbon and 10% crosslinking To Gelvatol 20-30 (40g) and gamma iron oxide (80g) was added water (300g). Then activated carbon (80g)

precoated with starch as described in Example 4 was stirred in to give a slurry. To this was added sufficient hydrochloric acid to give a solution pH of 1.5. The mixture was added to orthodichlorobenzene (3l) and Span 85 (90g) stirred at 1200 rpm with a three inch flat impeller in a baffled reactor. A solution of glutaraldehyde (9.2g, an amount calculated to react with and crosslink 10% of the hydroxy groups of the PVA) was added. After stirring for one hour, the slurry was filtered and the product washed with acetone followed by distilled water. The material was dried and cured to produce fine beads of about 50μm in size.

EXAMPLE 9

Preparation of a composite adsorbent material using polyacrylamide as the matrix To a solution of acrylamide (40g) in water (500 ml) were added methylene bisacrylamide (23.2g), carbon (80g) pretreated with glacial acetic acid according to Example 3, gamma iron oxide (80g) and Teric PE (4g). This aqueous suspension together with potassium persulphate (1g) was then added to Ondina 33 (300 ml) heated to 60° and mixed by stirring with Span 80 (3g). Samples were withdrawn at frequent intervals and when examination under the microscope indicated that the reaction was complete, the suspension was filtered and washed with hexane.

EXAMPLE 10

Preparation of a composite adsorbent material using a phenol formaldehyde resin as the matrix To a mixture of phenol (50g) and formaldehyde solution (37%, 108g) were added carbon (60g) precoated with glacial acetic acid according to the method of example 3 and gamma iron oxide (40g). Of this mixture, 110g was added to Ondina 33 (2l) and Span 80 (60g) and heated to 105° with vigorous stirring. After two hours the suspension was filtered and washed with hexane.

Before use of the composite materials of Examples 6–10, the protective layer was removed from the adsorbent by the approrpiate method described in Example 3 or 4.

EXAMPLE 11

Separation of isohumulones

This example illustrates the ability of the composite adsorbent material described in Example 5 to extract isohumulones. Experiments were carried out in which isohumulones were dissolved in phosphate buffer. The extractions were carried out by shaking the solution with the composite adsorbent material at various pH's through the use of added dilute phosphoric acid. The magnetic adsorbent was then recovered by decantation of the solution in the presence of an applied magnetic field (e.g. bar magnet). The efficiency of the extraction was determined by determining the amount of isohumulones remaining in the solution. This analysis was carried out by acidifying the solution to less than pH2, extracting it with isooctane and measuring the absorbence of the isooctane layer at 275 nm. A blank, consisting of an isohumulone-free buffer solution was treated in exactly the same way as the samples and was subtracted from each reading.

The experiments showed that at a pH below about 6, the isohumulones were extracted readily from the solution into the adsorbent.

EXAMPLE 12

Extraction of Riboflavin from aqueous solution

Magnetic adsorbent comprising 20% by weight of polyvinyl alcohol, 10% crosslinked with glutaraldehyde, 40% by weight of activated carbon and 40% by weight of gamma iron oxide was added to 100 ml of an aqueous solution of riboflavin (20 mg/l). The riboflavin was rapidly adsorbed as shown by testing the aqueous solution spectrophotometrically. The riboflavin was readily recovered either by treatment with aqueous acetic acid at pH 2 or by extraction with a 50% alcoholic alkali solution at pH 12.

EXAMPLE 13

Separation of Riboflavin from whey

Quantities of magnetic adsorbent as produced in Example 6 (0.3, 0.5 and 0.7g) were added to 50 ml. samples of 7% solids reconstituted cheese whey and shaken for one hour at room temperature. Trichloroacetic acid (20% solution, 10 ml) was added to each sample which were heated at 50° C. for one hour to precipitate protein. The samples were filtered and the filtrate analysed spectrophotometrically at 444mμ and 520mμ to determine residual riboflavin. The following results were obtained:

| TREATMENT | % RIBOFLAVIN ADSORBED |
|---|---|
| No treatment | 0 |
| 0.3 g magnetic composite | 54 |
| 0.5 g magnetic composite | 67 |
| 0.7 g magnetic composite | 75 |

EXAMPLE 14

Extraction of Streptomycin

This example illustrates the ability of the composite adsorbents to extract streptomycin from solution.

Solutions of streptomycin (0.2 and 0.3 mg/ml) were prepared in phosphate buffer at pH 6.8. 10 ml samples of the solutions were shaken for 45 minutes at room temperature with the composite adsorbent made in Example 6. The residual amount of streptomycin was determined by a method (J. Biol. Chem. 169 153 (1947)) involving boiling a sample of the supernatant liquid in 0.4M sodium hydroxide for three minutes, cooling and acidifying and determining the optical density at 275mμ. It was found that 1g of the composite adsorbent extracted 97% of the streptomycin from the solution containing 0.2 mg/ml. Studies on the rate of adsorption showed that it was substantially complete after 30 minutes.

Recovery of the streptomycin from the composite adsorbent was achieved readily by treatment with methanol acidified with hydrochloric acid, or preferably acetic acid, or with 10% acetone acidified to pH 2.5 with sulphuric acid.

EXAMPLE 15

Extraction of Penicillin G

This example demonstrates the capability of the composite adsorbent to extract penicillin from solution.

The method of Example 14 was carried out using a solution containing 0.25 mg/ml of penicillin G. The penicillin was extracted more slowly than the streptomycin and 52% was adsorbed after 130 minutes by 1g of the adsorbent in 10 ml of solution. The adsorption was determined by the method of J. Biol. Chem. 1964 725 (1964) in which the supernatant liquid was heated in acetate buffer (pH 4.6) and water and the optical density at 322mμ determined. The penicillin was removed from the adsorbent using acetone containing 15% water.

EXAMPLE 16

Demonstration of the selectivity of the magnetic composite materials

The ability to control the selectivity of the magnetic composite materials lies mainly in the selection of the adsorbent which is enclosed in the matrix and the degree of crosslinking of the matrix. The latter allows a range of pore size to be produced in the matrix. Thus, with a low degree of crosslinking, large pore sizes are produced which permit the infiltration of larger molecular weight materials while a high degree of crosslinking restricts the pore size thus excluding the higher molecular weight materials and permitting lower molecular weight species to enter the matrix. This effect was demonstrated by observing the adsorption of riboflavin, which has a molecular weight of 376, with that of naphthol green which has a molecular weight of 878. Composite adsorbent materials with different degrees of crosslinking were used. As shown in FIGS. 1 and 2, there is a striking difference in adsorption when the adsorbent is crosslinked more than 30–40%. Above this level, the adsorption of naphthol green is considerably reduced and is effectively nil with a 100% crosslinked material. Further confirmation of this effect was obtained by adding a sample of magnetic composite adsorbent material in which the polyvinyl alcohol matrix was crosslinked 100% with glutaraldehyde to a solution containing both riboflavin (10 mg/l) and naphthol green (20 mg/l). On equilibration it was found that all of the riboflavin had been adsorbed but the aqueous concentration of the naphthol green remained unaltered.

EXAMPLE 17

Adsorption of a surfactant by a magnetic composite material

This example illustrates the ability of the composite materials to remove small traces of undesirable materials, such as surfactants, in the control of pollution.

An aqueous solution of sodium dodecylbenzene sulphonate (20 mg/l, 100 ml) at pH 4.0 was mixed with magnetic composite containing 20% by weight of polyvinyl alcohol, 40% of gamma iron oxide and 40% of aluminium oxide (1g). After agitation for 30 minutes, more than 90% of the surfactant had been removed from the solution as measured by UV spectrophotometry at 224mμ. The adsorbed surfactant could be readily desorbed by washing with weak alkali ($10^{-2}$M sodium hydroxide), leaving the composite material in a regenerated state for further adsorption.

EXAMPLE 18

Extraction of Tryptophan from aqueous solution

To an aqueous solution of tryptophan (0.4 mg/ml; 10 ml) at pH 6.4 was added magnetic composite adsorbent material incorporating silica gel (40% by weight) as adsorbent, prepared according to the method of example 6. The mixture was stirred for four hours and the supernatant liquid analysed for tryptophan by UV spectrophotometry at 255mμ. This indicated that 25% of the tryptophan had been adsorbed.

EXAMPLE 19

To 1g of a lightly crosslinked (10%) magnetic composite adsorbent containing 40% carbon, prepared as described in example 8, was added 20 ml of a 40 mg/l solution of vitamin $B_{12}$. The suspension was shaken for two hours and the supernate analyzed by ultraviolet spectroscopy; vitamin $B_{12}$ has a characteristic peak at wavelength 375mμ. The results showed 100% uptake of vitamin $B_{12}$ by the magnetic adsorbent. Composite adsorbent materials in which the matrix was crosslinked to 30% and 50% were found to adsorb vitamin $B_{12}$ to a far less extent.

EXAMPLE 20

Removal of isohumulone from spent brewers yeast

Yeast suspension (500 ml, containing 80g of solids) was added to 10g of 30% crosslinked magnetic composite material containing carbon and prepared according to the method of example 6. It was stirred and heated at 50° C. then the supernatant liquor sampled initially and after one and two hours. The samples were analysed by acidifying 10 ml aliquots with hydrochloric acid and extracting the residual isohumulone with 25 mls of 2:2:4 trimethyl pentane.

The 2:2:4 trimethyl pentane layer was sampled by taking a 10 ml aliquot from which the isohumulone was extracted with pH 7.45 0.05M phosphate buffer (50 ml). The 2:2:4 trimethyl pentane layer was discarded and replaced with a further 10 mls of 2:2:4 trimethyl pentane, the phosphate buffer layer acidified with hydrochloric acid and the isohumulone extracted into the 2:2:4 trimethyl pentane layer. It was analysed spectrometrically at 254 and 275mμ and found that 98% of the isohumulone had been adsorbed in one hour.

The composite material was regenerated with 0.1M sodium hydroxide in 60% methanol/40% water.

A number of proprietary materials are referred to in the above examples. A list of these with descriptions of their source and nature is as follows:

Gelvatol 20-30 — Polyvinyl alcohol (PVA); nominally 88% hydrolysed and of low molecular weight; supplied by Monsanto Coy.

Polymid 55 — A hydrophobic polyamide derived from fatty acids; supplied by Polymer Corp.

Corvis — A copolymer of vinyl chloride (98%) and vinyl acetate (2%); supplied by ICI Ltd.

Glutaraldehyde — 25% aqueous solution; supplied by Union Carbide Corp.

Span 80 — Sorbitan mono-oleate with HLB 4.3; supplied by ICI Ltd.

Span 85 — Sorbitan trioleate with HLB 1.8; supplied by ICI Ltd.

Teric PE 68 — Dispersant with HLB 24.0; supplied by ICI Ltd.

Ondina 33 — Hydrocarbon oil, SG 0.888; supplied by Shell.

Gamma Iron Oxide — $\gamma$-$Fe_2O_3$, needle shaped pigment of about 0.1μm particle size; supplied by Bayer as S11.

Black Iron Oxide — $Fe_3O_4$; supplied by Bayer as 318M.

Carbon — Activated carbon used widely in the food industry; supplied by ICI as DARCO G60.

Aluminium oxide — Alumina, 100–200 mesh, desiccant grade; supplied by Griffin and George Ltd.

Silica Gel — 100–200 mesh, chromatographic grade; supplied by Hopkins and Willians Ltd.

We claim:

1. A composite adsorbent material for adsorbing dissolved organic materials of up to a predetermined molecular weight from solution comprising adsorbent particles and magnetic particles embedded in a porous matrix of a partially or wholly cross-linked hydrophilic polymer, the degree of cross-linking being selected to provide a porosity to allow only molecules of up to said predetermined molecular weight to enter into the interstitial structure of the matrix and to exclude molecules of higher molecular weight whereby the composite adsorbent material may function selectively to adsorb dissolved organic materials of up to said predetermined molecular weight from solution.

2. A composite material as claimed in claim 1 when in the form of beads.

3. A composite material as claimed in claim 1 in which the adsorbent particles are selected from carbon, alumina, silica gel, activated magnesium silicate, clays or mineral powders, the particles being embedded in the porous matrix in such a way that a large proportion of their surface area retains the capability of adsorbing the dissolved organic material to be separated.

4. A composite material as claimed in claim 1 in which the magnetic particles are precoated with a thin, insoluble and protective layer to prevent the magnetic particles from being dissolved during usage of the composite material.

5. A composite material as claimed in claim 4 in which the protective layer is an organic polymeric material.

6. A composite material as claimed in claim 1 in which the adsorbent particles are precoated with a protective layer prior to incorporation in the composite material, such protective layer being subsequently removed to reactivate the adsorbent particles.

7. A composite material as claimed in claim 4 in which the adsorbent particles are precoated with a protective layer prior to incorporation in the composite material, such protective layer being subsequently removed to reactivate the adsorbent particles.

8. A composite material as claimed in claim 6 in which the protective layer is an aliphatic acid, starch or gelatine.

9. A composite material as claimed in claim 7 in which the protective layer is an aliphatic acid, starch or gelatine.

10. A composite material as claimed in claim 1 in which the porous matrix comprises cross-linked polyvinyl alcohol.

11. A composite material as claimed in claim 1 in which the porous matrix comprises cross-linked polyacrylamide or phenol formaldehyde.

12. A method of making a composite selective adsorbent material for adsorbing dissolved organic materials of up to a predetermined molecular weight from solution comprising the steps of mixing adsorbent particles and magnetic particles with polymerisable material capable of forming a partially or wholly cross-linked hydrophilic polymer and a cross-linking agent, and controlling the degree to which crosslinking of the polymerisable material occurs whereby a porous partially or wholly cross-linked polymeric matrix incorporating the adsorbent particles and the magnetic particles is produced in which the pore size is such as to allow only molecules of up to a predetermined molecular weight to enter into the interstitial structure of the matrix and to exclude molecules of higher molecular weight, the composite adsorbent material thus being capable of selectively adsorbing dissolved organic materials of up to the predetermined molecular weight from solution.

13. A method as claimed in claim 12 in which the magnetic particles are precoated with a thin, insoluble and protective layer before they are incorporated into the mixture.

14. A method as claimed in claim 12 in which the adsorbent particles are precoated with a protective layer before they are incorporated into the mixture.

15. A method as claimed in claim 14 in which the precoated adsorbent particles, a dispersion or solution of the polymerisable material capable of forming the partially or wholly cross-linked hydrophilic polymer, the crosslinking agent, the magnetic particles, a surfactant and a liquid which forms a separate phase with the liquid in said dispersion or solution are mixed to form a slurry, the slurry is stirred to produce a product in the form of beads, and the adsorbent particles are reactivated by removal of their protective coating.

16. A method as claimed in claim 14 in which a slurry is formed by mixing polyvinyl alcohol dissolved in water, precoated adsorbent particles, the magnetic particles, and the crosslinking agent, the slurry thus formed is added to an organic liquid which forms a separate phase with water, and the resultant mixture is stirred in a manner appropriate to produce a product in the desired physical form.

* * * * *